(12) United States Patent
Ismail et al.

(10) Patent No.: US 10,907,107 B1
(45) Date of Patent: *Feb. 2, 2021

(54) AMPHIPHILIC ASPHALTENE IONIC LIQUIDS AS DEMULSIFIERS FOR HEAVY PETROLEUM CRUDE OIL-WATER EMULSIONS

(71) Applicant: King Abdulaziz University, Jeddah (SA)

(72) Inventors: Ali Issa Ismail, Jeddah (SA); Ayman Mohamady Atta, Jeddah (SA); Mohamed Hassan El-Newehy, Jeddah (SA); Mohamed E. EL-Hefnawy, Jeddah (SA)

(73) Assignee: King Abdulaziz University, Jeddah (SA)

(*) Notice: Subject to any disclaimer, the term of this patent is extended or adjusted under 35 U.S.C. 154(b) by 15 days.

This patent is subject to a terminal disclaimer.

(21) Appl. No.: 16/894,975

(22) Filed: Jun. 8, 2020

Related U.S. Application Data

(62) Division of application No. 16/750,041, filed on Jan. 23, 2020.

(51) Int. Cl.
| | | |
|---|---|---|
| *C10G 33/04* | (2006.01) |
| *C07D 495/22* | (2006.01) |
| *B01D 17/04* | (2006.01) |
| *C07C 7/20* | (2006.01) |
| *B01D 11/02* | (2006.01) |

(52) U.S. Cl.
CPC .......... *C10G 33/04* (2013.01); *B01D 11/0292* (2013.01); *B01D 17/047* (2013.01); *C07C 7/20* (2013.01); *C07D 495/22* (2013.01); *C10G 2300/206* (2013.01)

(58) Field of Classification Search
CPC .... C10G 2300/206; C10G 33/04; C07C 7/20; B01D 11/0292; B01D 17/047; C07D 495/22
See application file for complete search history.

(56) References Cited

U.S. PATENT DOCUMENTS

| | | | | |
|---|---|---|---|---|
| 9,169,446 | B2 * | 10/2015 | Yusuf | C10G 33/08 |
| 9,212,159 | B1 * | 12/2015 | Siddiqui | C07D 333/76 |
| 10,131,556 | B1 * | 11/2018 | Atta | B01J 20/3295 |
| 10,723,957 | B1 * | 7/2020 | Ismail | C10G 21/20 |
| 2015/0315486 | A1 * | 11/2015 | Yusuf | C10G 33/04 516/141 |
| 2017/0284605 | A1 * | 10/2017 | Janak | C11D 3/28 |
| 2020/0017790 | A1 * | 1/2020 | Weers | C09K 15/30 |
| 2020/0071265 | A1 * | 3/2020 | Dhawan | C09K 8/584 |

* cited by examiner

*Primary Examiner* — Michael A Salvitti
(74) *Attorney, Agent, or Firm* — W&C IP

(57) ABSTRACT

Provided herein are amphiphilic asphaltene ionic liquids and methods of making and using the amphiphilic asphaltene ionic liquids, e.g. as demulsifiers for petroleum crude oil-water emulsions.

3 Claims, 9 Drawing Sheets
(9 of 9 Drawing Sheet(s) Filed in Color)

AMPHIPHILIC ASPHALTENE IONIC LIQUIDS AS DEMULSIFIERS FOR HEAVY PETROLEUM CRUDE OIL-WATER EMULSIONS

BACKGROUND OF THE INVENTION

Field of the Invention

This invention generally relates to new amphiphilic asphaltene ionic liquids. The amphiphilic asphaltene ionic liquids are used as demulsifiers for petroleum crude oil-water emulsions.

State of Technology

Asphaltenes are highly polycondensed aromatic, high molecular weight constituents contained in many crude petroleum residual and natural asphalts. Changes in pressure and temperature during processing of crude oil occur and cause asphaltenes to destabilize and precipitate, forming problematic hard black deposits (asphalt) in pipes, pumps and vessels. Substances intended to improve polymeric flow can be used to address this problem, and asphaltene components can be made more responsive to polymeric flow improvers by either adding them directly to the oil, or first combining asphaltene with the flow improver and adding the combination to the oil in the field, e.g. as oil-field chemicals [1].

Different oxidizing agents such as permanganate compounds, cerium compounds, chromate compounds, dichromate compounds, peroxide compounds, ozone, tetroxide compounds, nitrate compounds, nitrite compounds, persulfate compounds, peroxy acids, halogen-containing compounds (e.g., hypochlorite, chlorite, chlorate, perchlorate and analogous halogen-containing compounds) and derivatives have been used to oxidize asphaltene to produce new compatible oil-field chemicals [2]. Asphaltenes that would otherwise precipitate and separate from viscous asphaltenic crude oils can be converted to mobile asphaltene-conversion products and mixed with at least the maltene components of the crude oils to form pumpable liquid oil products [3]. Asphaltene can also be reacted with phosphorous trichloride to produce a phosphochlorinated-asphaltene and modified with equimolar amounts of aliphatic or aromatic amines and polyamines to make them suitable to apply as oil-field chemicals [4]. Moreover, the phosphochlorinated-asphaltene can be reacted with polypropylene oxide to produce amphiphilic surfactants that act as asphaltene dispersents for heavy crude oil [5]. The asphaltene can also be converted to anionic surfactants by sulfonation and used as capping for magnetite, e.g. for use as oil spill collectors for heavy crude oil [6-7]. Asphaltenes can also be converted to nonionic surfactants by reacting them with maleic anhydride followed by neutralization with metal (II) oxides or hydroxides and then applied as emulsifier and dispersing agents [8]. In addition, asphaltenes can be injected into oil formations via the injection well as sacrificial agents to inhibit the deposition of chemical recovery agents such as surfactant on the reservoir matrix [9].

Ionic liquids (ILs) and poly (ionic liquids), PILs, are organic salts based on imidazolium, pyridinium, and quaternary ammonium cations having a low melting point, non-flammable, and higher thermal stability have been used in the petroleum industry [10]. IL formulations based on amines, block copolymers and hydrophobic ILs (1,5-dicarboxy-pentane-2-ammonium, pyridinium, isoquinolinium, imidazolium, ammonium and ammonium carboxymethane, and an anion such as $R_5COO^-$, $Cl^-$, $Br^-$, $[BF_4]^-$, $[PF_6]^-$, $[SbF_6]^-$, $[R_6SO_4]^-$, $[OTs]^-$, $[OMs]^-$, etc. have been used to demulsify, dehydrate and desalt crude oil [11]. Alkyl ammonium ionic liquids are known to reduce the interfacial tension of crude oil-water systems and are used for enhanced oil recovery via an ionic liquid-polymer flooding technique [12].

There is a need in the art to further improve technologies related to demulsifying heavy petroleum crude oil-water emulsions.

SUMMARY OF THE INVENTION

The present disclosure describes modifications of the chemical structure of asphaltenes which have been separated from crude oil, asphalt and/or petroleum sludge. The asphaltenes are modified to produce amphiphilic ILs and PILs. The modifications are performed via carboxylation of asphaltenes, followed by the formation of asphaltene acid chlorides from the carboxylated asphaltenes. The carboxylated asphaltenes are then reacted with n-ethoxylated alkyl pyridinium derivatives to form the amphiphilic asphaltene ILs and PILs. The new amphiphilic asphaltene ILs and PILs, which exhibit many structural variations, have been successfully used to demulsify petroleum crude oil-water (e.g. sea water) emulsions. The amphiphilic asphaltenes are also used as asphaltene stabilizers for crude oil. As stabilizers, they prevent the aggregation and precipitation of asphaltenes from the oil, facilitating storage and transport. In addition, they are used as agents to modify the viscosity of crude oil, thereby enhancing oil recovery from, e.g., heavy and extra-heavy crude oil.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

It is an object of this invention to modify the chemical structure of asphaltenes that are separated from crude oil, asphalt and petroleum sludge to produce amphiphilic ionic liquids (AILs). The AILs were prepared through carboxylation of asphaltene either by oxidation or reaction with maleic anhydride (MA) to obtain asphaltene carboxylic acid adducts (ACA) or asphaltene maleic anhydride adducts (AMA), respectively. ACA or AMA may be reacted with thionyl chloride ($SOCl_2$) to produce asphaltene acid chloride (As—COCl) that is reacted with quaternized N-ethoxylated alkyl pyridinium salts (QAP-S). The modified new AILs were used to replace asphaltene layer on the emulsified water droplet to demulsify the petroleum crude oil emulsions.

It is another object of this invention to provide a method of forming asphaltene quaternary aminopyridine salts for use as amphiphilic asphaltene ionic liquids which are useful in demulsifying petroleum crude oil-water emulsions, in stabilizing petroleum crude oil, and in other applications. The asphaltene quaternary aminopyridine salts may be made by i) oxidizing alkyl chains of asphaltenes to form asphaltene carboxylic acids; forming halide salts of the asphaltene carboxylic acids, and reacting the halide salts with quarternary ethoxylated aminopyridine to form the asphaltene quaternary aminopyridine salts;

or ii) reacting the asphaltene with malic anhydride to form asphaltene malic anhydride adducts (AMA) which have one or more carboxylic acids on a periphery of the AMA molecules, forming halide salts of the one or more carboxylic acids, and reacting the halide salts with quartenary ethoxylated aminopyridine to form the asphaltene quaternary aminopyridine salts;

or iii) reacting the asphaltene with malic anhydride to form asphaltene malic anhydride adducts (AMA) which have one or more carboxylic acids on a periphery of the AMA molecules, and reacting the asphaltene malic anhydride adducts with the quartenary ethoxylated aminopyridine to form the asphaltene quaternary aminopyridine salts.

In these methods, the asphaltene quaternary aminopyridine salts may have Br, $CH_3COO$, OCN, $H_2PO_4$), $HSO_4$, $SCN$, $NO_3$, $PF_6$, $BF_4$, $HCO_3$, or $CF_3SO_2)_2N$ anions. An exemplary quaternary ethoxylated pyridine used to make the asphaltene quaternary aminopyridine salts is quaternized ethoxylated alkyl pyridinium bromide (QEAP).

The asphaltene quaternary aminopyridine salts made with one crude oil may be recycled and used to stabilize or demulsify other crude oils.

An exemplary asphaltene quaternary aminopyridine salt is

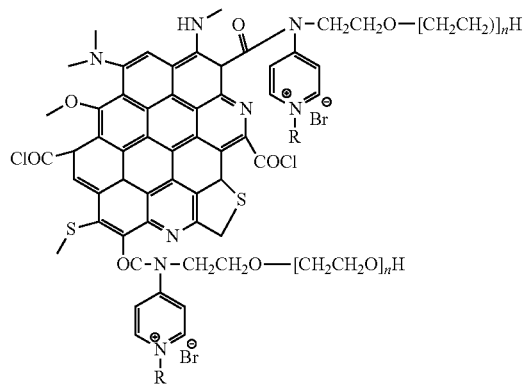

where R is $C_5H_{11}$ to $C_{22}H_{45}$ and may be the same or different at different locations. Another exemplary quaternary aminopyridine salt is

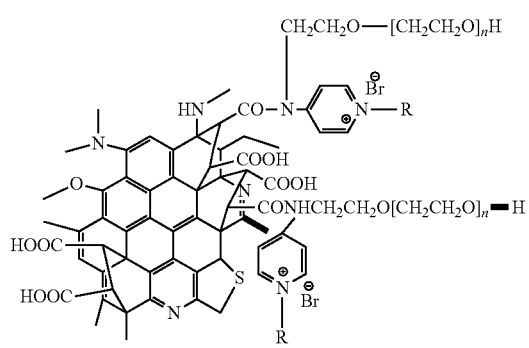

where R is $C_5H_{11}$ to $C_{22}H_{45}$ and may be the same or different at different locations.

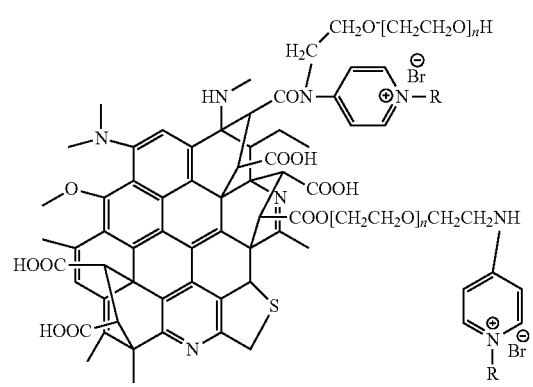

where R is $C_5H_{11}$ to $C_{22}H_{45}$ and may be the same or different at different locations.

Figure 1:
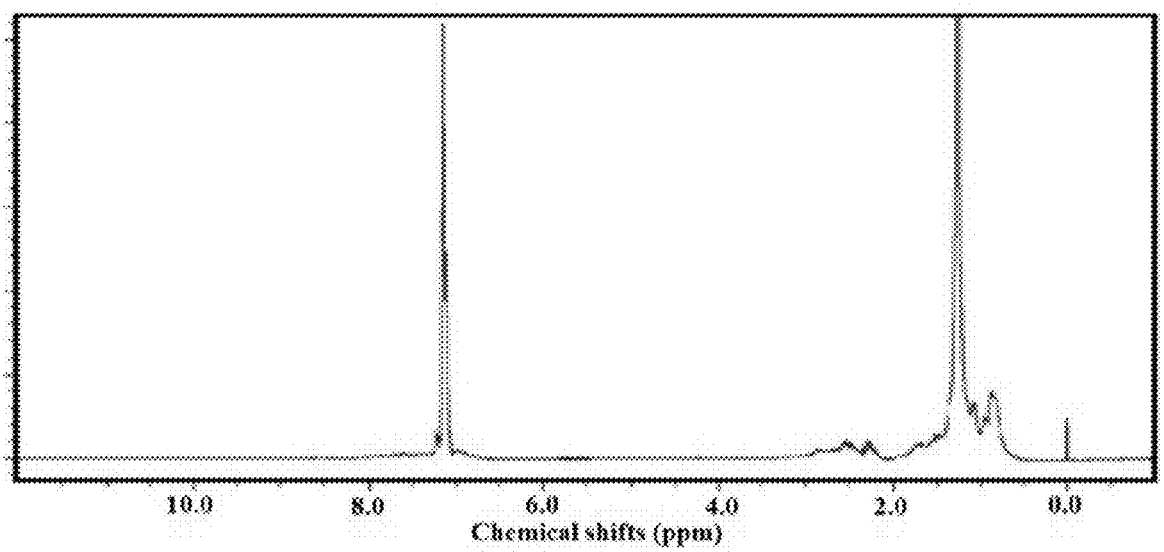
FIG. 1. HNMR spectrum of asphaltenes.

The patent or application file contains at least one drawing executed in color. Copies of this patent or patent application publication with color drawings will be provided by the Office upon request and payment of the necessary fee.

DETAILED DESCRIPTION

The present disclosure describes new amphiphilic asphaltene ionic liquids (AILs), referred to herein as AIL, AIL-1, AIL-2, etc. The ILs and PILs may be referred to collectively as "AIL, AIL-1, or AIL-2", in that ILs and PILs are treated as one and the same in terms of their manufacture and use according to the embodiments of the invention. The new compounds are used to demulsify crude oil/water emulsions and/or to stabilize crude oil. The compounds are advantageously reusable or recyclable. For example, after use in one crude oil emulsion, they can be reclaimed/recovered and used to demulsify another crude oil emulsion, and so on so that they are used repeatedly.

In some aspects, the AILs (which may be referred to herein as "AIL type 1" or "AIL-1") are formed by oxidation of alkyl chains on the periphery of asphaltenes to form carboxylic groups, thereby forming asphaltene carboxylic acids (ACA). This step is referred to herein as "Method 1". The ACA is then converted to acid chloride (e.g. acid chlorides, "As—COCl"), this step being referred to herein as "Method 3". Finally, the As—COCl is reacted with a quaternized ethoxylated alkyl pyridinium salts (QAP-S) salt, such as bromide salt (QEAP), to form amphiphilic asphaltene ionic liquids (AIL-1), this latter step being referred to herein as "Method 4". In particular, trimethylamine is used as a catalyst for the reaction referred herein as "Method 4".

Scheme 1 is an exemplary depiction of a combination of reactions conducted using Methods 1 and 3; Scheme 2 is an exemplary depiction of the conversion of As—COCl to amphiphilic asphaltene ionic liquid (AIL-1) by reacting the As—COCl with QEAP using trimethylamine as a catalyst (Method 4).

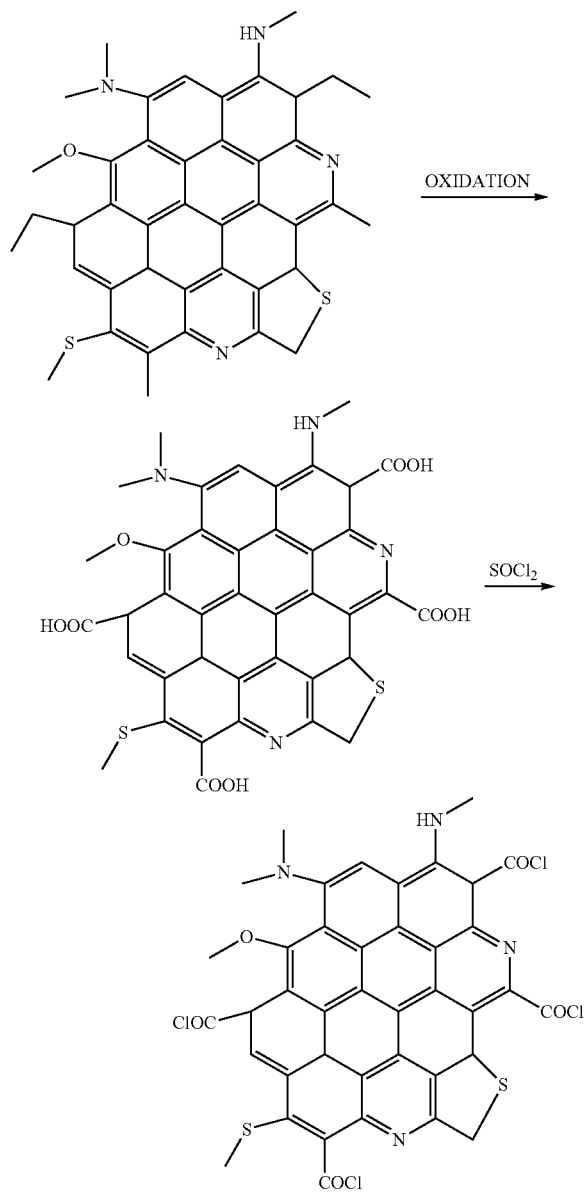

Scheme 1:
Synthesis of exemplary As-COCl using Methods 1 and 3.

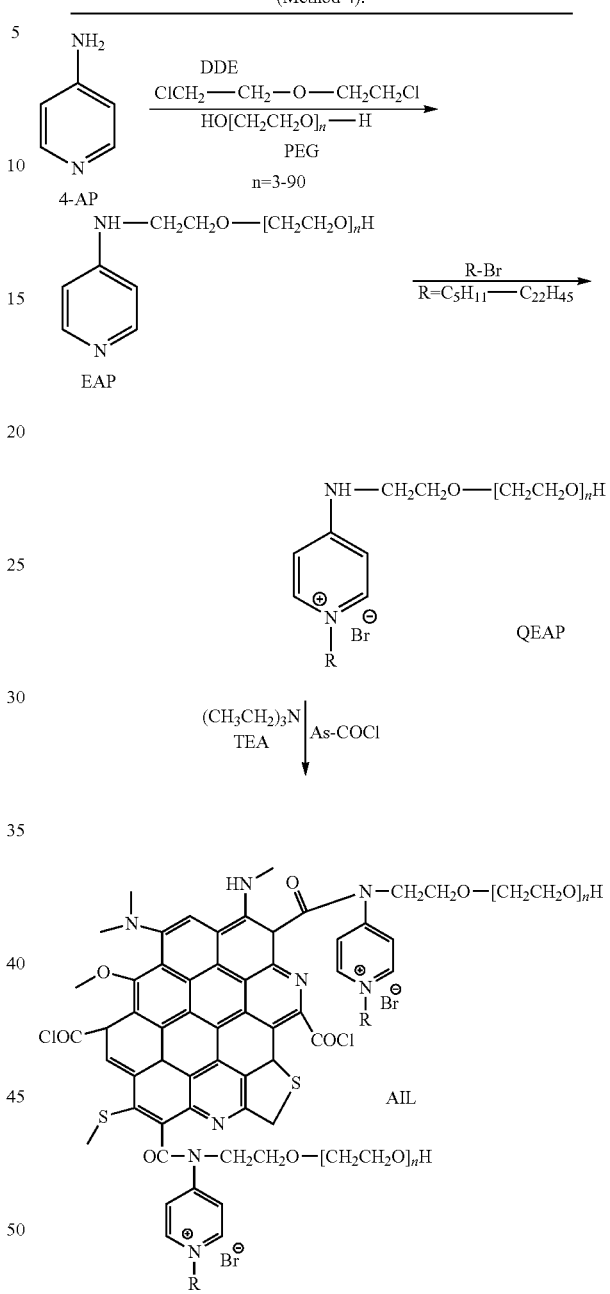

Scheme 2.
Reacting As-COCl with QEAP using trimethylamine as a catalyst (Method 4).

In short, AAC changed to As—COCl in scheme 2.

In a second aspect, a different set of AILs ("AIL type 2" or "AIL-2") was prepared after reacting asphaltenes with e.g. maleic anhydride to form asphaltene/maleic anhydride adducts (AMA), which, like the ACA described above, also have peripheral COOH groups, which are derived from the maleic anhydride. This synthesis reaction is referred to herein as "Method 2". This reaction is followed by esterification or amidation with QAP-S e.g. QEAP in the presence of EDC (referred to herein as "Method 5"). The set of reactions to form AIL-2 is shown in Scheme 3.

Method 3 converts both ACA and AMA to As—COCl through reacting with $SOCl_2$.

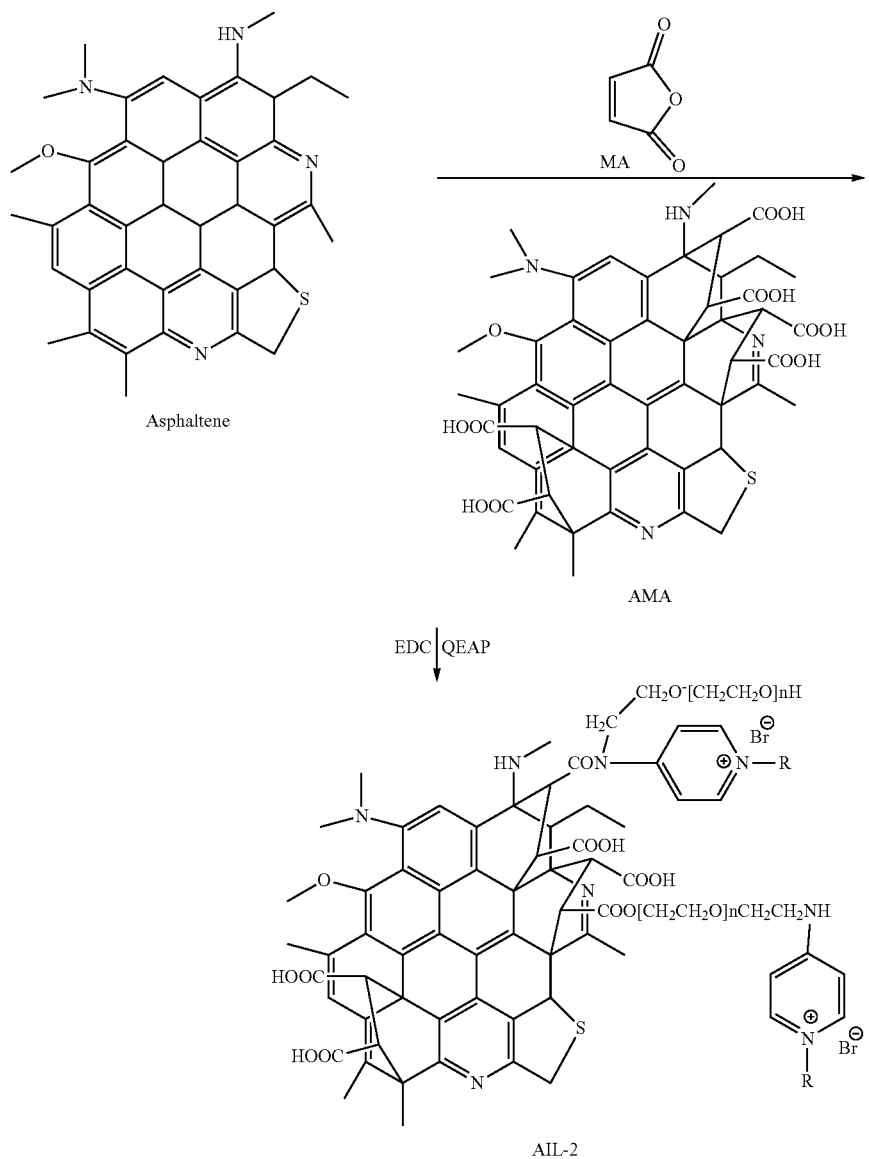

Scheme 3.
Synthesis of AIL-2 using methods 2 and 5.

Method 1

Method 1 refers to the oxidation of alkyl chains on the periphery of asphaltenes, converting them to carboxylic groups and forming asphaltene carboxylic acids (ACAs). This step of oxidation may be performed e.g. by acidifying the asphaltenes by exposure to a strong acid (e.g. sulfuric acid, nitric acid or phosphoric acid) and then exposing the asphaltenes to an oxidizing agent such as $KMnO_4$ or $K_2Cr_2O_7$ or $K_2CrO_4$) as described in the Examples section below. Such reactions are generally performed e.g. at a temperature ranging from about 1 to about 25° C., such as at about 1, 5, 10, 15, 20 or 25° C., and generally with constant stirring or agitation, followed by heating to e.g. from about 25 to 90° C., such as to about 30 to 80° C., e.g. about 30, 35, 40, 45, 50, 55, 60, 65, 70, 75, or 80° C., for about 20-60 minutes, e.g. about 20, 30, 40, 50, or 60 minutes). Further steps may include e.g. dilution (e.g. using $H_2O$), further reacting the diluted mixture at an elevated temperature such as about 50-120° C. (about 50, 60, 70, 80, 90, 100, 110, or 120° C.) for about 5-45 minutes, e.g. about 5, 10, 15, 20, 25, 30, 35, 40 or 45 min, such as, for example, 15 min. The reaction can be stopped e.g. by the addition of hydrogen peroxide (e.g. a 30% solution); this may be done after further dilution e.g. with $dH_2O$. Further steps of washing (e.g. in a mild acidic solution), filtering, drying, sonication, centrifugation, etc., and others known in the art, may be undertaken to isolate the reaction products.

However, other methods of oxidizing the alkyl chains on the periphery of asphaltenes to form ACAs may be used, including but not limited to: A 50 mL Erlenmeyer Asphaltene (1 g), $Na_2Cr_2O_7.2H_2O$ (1.47 mmol)) and 2.5 mL of glacial acetic acid were added into flask 50 mL and heated to 100° C. on the hot plate. Once the reaction has reached temperature, turn off the heat and allow the reaction to cool to at least 80° C. before continuing. Add 0.8 mL of $H_2SO_4$ dropwise very carefully. Be sure to swirl the flask after every few drops to affect mixing. Once addition is complete, heat the flask back up to 100° C. for 5 min. Remove the flask from heat and allow it to cool slightly. Add 0.3 mL of ethanol dropwise to the solution. Slowly add water to the solution with continuous swirling until the total volume reaches ~35 mL. Heat the solution at 100° C. for 10 min to aid in dissolving impurities. Allow the solution to cool until the flask can be handled easily (~5 min). Collect the solid product via Hirsch filtration. Wash the product with 10 mL of cold water or until an off-white solid is obtained. Recrystallize the solid from a minimum volume of hot ethanol. Collect the crystals via Hirsch filtration.

Method 2

As described above, a second reaction pathway involves reaction of asphaltene with malic anhydride (MA) to form AMA adducts, (AMAs) which contain the carboxyl groups of the MA and are thus also technically "asphaltene carboxylic acids". This reaction is generally performed e.g. in a suitable solvent such as toluene via refluxing under $N_2$ at reaction temperature ranged from 100 to 180° C. for e.g. 6-20 hours, such as for 8 hr. The solvent is then removed to yield the AMA adducts.

The AMAs may then also undergo a Method 3 reaction, as described below.

Method 3

The ACAs and/or the AMAs are converted to acid chloride. This may be done by any suitable method, examples of which include but are not limited to: mixing the ACAs OR AMAs with a halide ion donor such as $SOCl_{12}$, or $PCl_3$ or $PCl_5$ or using dry toluene containing catalytic amount of pyridine, the oxalyl chloride).

The corresponding asphaltene acid chloride salt is formed and hazardous HCl or $POCl_3$ etc were formed during using $PCl_3$ or $PC_5$. Reaction conditions are generally known in the art, e.g. refluxing at room temperature for e.g. 6-20 hours, such as for 6, 8, 10, 12, 14, 16, 18 or 20 hours.

Methods 4 and 5

The asphaltene acid chloride As—COCl formed in Method 3 and AMA formed in Method 2 are then reacted with a quaternized ethoxylated alkyl pyridinium salts (QAP-S) such as bromide salt (QEAP), to form the amphiphilic asphaltene ionic liquids (AILs) using one of two methods, Method 4 or Method 5 (see Examples section). The reaction of As—COCl with QAP-S was catalyzed with trimethylamine (TEA) as described in Method 4 (see Examples section). The resulting product is a type I AIL (AIL-1) and is recovered using methods known in the art.

Alternatively, the ACA and AMA can be reacted with QAP-S in the presence of a carbodiimide crosslinking reagent (for example, 1-Ethyl-3-(3-dimethylaminopropyl) carbodiimide (EDC) as catalyst (Method 5) as shown in Scheme 3 to yield a type 2 AIL (AIL-2). This reaction is also performed in a suitable solvent such as chloroform, methylene chloride carbon tetrachloride. In such a system, AMA are reacted with a QAP-S e.g. QEAP at a temperature of from about 5-30 degrees, such as about 1, 5, 15, 20, 25, or 30° C., for a suitable time period, e.g. about 6 to 24 hours, such as for about 6, 8, 10, 12, 14, 16, 18, 20, 22 or 24 hours. Removal of solvent and precipitation (e.g. in a hydrophobic solvent such as heptane) yields the type 2 reactions products, AIL-2.

The QAP Salts

In some aspects, the QAP-S that is employed is bromide salt (QEAP), the synthesis of which is described in the Examples section below. However, other QAP salts may also be used, some of which are formed by replacement of Br from QEAP with another anion, e.g. $CH_3COO^-$, $OCN^-$, $H_2PO_4^-$, $HSO_4^-$, $SCN^-$, $NO_3^-$, $PF_6^-$, $BF_4^-$, $HCO_3^-$, $(CF_3SO_2)_2N^-$, to obtain a different QAP-S, which is then reacted with As—COCl or AMA to form an AILs. These varying AIL salts may be advantageous due to having differing properties, such as different melting temperatures. In some aspects, the melting temperatures range e.g. from about 40 to 85° C., such as about 40, 45, 50, 55, 60, 65, 70, 75, 80, or 85° C. The variation of melting temperatures of the prepared AILs below 100° C. elucidates that the prepared derivatives are organic salts of ILs and they are not cationic amphiphiles.

Methods of Using the AIL (AIL-1 and AIL-2)

Demulsification of crude oil is the breaking or destabilization of a crude oil emulsion into separate oil and water phases. Embodiments of the invention can be practiced with any crude oil containing water, or especially containing saltwater (brine), in some aspects it is practiced with heavy or waxy crude oils. Heavy or waxy crude oils have one or more of the following characteristics: The crude oil has an API gravity ranging from about 5 to about 30. The crude oil has a high naphthenic acid concentration, and is characterized by a high "TAN" number (the TAN number represents the number of milliequivalents of potassium hydroxide required to neutralize 1 gram of crude oil). The asphaltene fraction of the crude oil soluble in toluene and precipitated in n-heptane ranges from about 0.5 wt. % to about 15 wt. %. In addition, embodiments of the invention can also be practiced on crude oil distillates, synthetic oils, silicon oils and vegetable or animal derived oils, if needed.

To practice the methods, an effective amount of one or more or the AILs disclosed herein (a demulsifier formulation) is combined with the crude oil emulsion. An effective amount of the formulation is, for example, the amount necessary to displace the surface-active component from the water droplets in the emulsion and render the water droplets more amenable to coalescence. The effective amount ranges from about 5 ppm to about 10,000 ppm based on the weight of the crude oil, with about 100 ppm to about 5000 ppm being preferred.

Demulsification of a crude oil sample involves the coalescence of e.g. dispersed seawater droplets by the addition of an effective amount of one or more of the AILs described herein. The process is generally performed by thorough mixing of the crude oil and the additive, e.g., by agitation. This process of coalescence may be further enhanced by other techniques, e.g. the application of electrostatic fields, and/or centrifugation or hydrocyclone treatments, and by performing the reaction at an elevated temperature, e.g. about 50-75° C., such as about 60-65° C.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

In the description above, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

Examples

Experimental

Materials:

Bitumen Saudi Arabia was used as a source of asphaltene and its properties are given in Table 1. Asphaltene was separated from petroleum crude oil sludge (50 g) by Soxhlet extraction with toluene (300 mL) followed by rotary evaporation to obtain toluene soluble organics (TSO) (bituminous like material). The remaining solid toluene insoluble organics in the Soxhlet funnel (TIM) was re-extracted with 150 ml of tetrahydrofuran (THF) for 3 hr and THF was evaporated and the weight of heavy asphaltene fraction (HAs). The TSO was wetted with benzene or toluene and 100 ml of the alkane solvent (n-pentane or n-heptane) was added. The precipitated organics (insoluble) were filtered and dried 2 h at 105° C., as light asphaltene fractions. Toluene:n-heptane solvents (1:40 vol %) were used to isolate the asphaltene fractions from crude oil. Arabic heavy crude oil (19.2° API) and medium crude oil (30.8 API) were produced from Ras Gara Aramco, Saudi Arabia. Seawater was collected from the Arabian Gulf. 4-Aminopyridine (4-AP), ethylene glycol, diethylene glycol, triethylene glycol, tetraethylene glycol and polyethylene glycols (PEG) having different ethoxy groups ranged from 3 to 90 were purchased from Sigma-Aldrich and used as received. Alkyl bromides (R—Br) based on pentyl, hexyl, heptyl, octyl, dodecyl, tetradecyl, octadecyl and docosyl bromide were obtained from Merck Co. and used to quaternize 4-AP. Dichlorodiethyl ether (DDE), 1-ethyl-3-(3-dimethylaminopropyl) carbodiimide (EDC), maleic anhydride (MA), hydrogen peroxide, $KMnO_4$, concentrated sulfuric acid and organic solvents were obtained from Sigma-Aldrich and used as received. Heavy and medium Saudi crude oil was provided from Ras Tanura oil field, Aramco, Saudi Arabia with the specifications listed in Tables 2 and 3.

TABLE 1

Asphalt properties and test method.

| Asphalt properties<br>Crude source: Saudi Arabia | Value | Method |
|---|---|---|
| Density @ 15° C./gcm$^{-3}$ | 1.034 | JTJ 052 T0603-1993 |
| Penetration @ 25° C./0.1 mm | 68.0 | JTJ 052 T0604-2000 |
| Softening point (° C.) | 48.5 | JTJ 052 T0606-2000 |
| Viscosity at 60° C./Pa s | 218.2 | JTJ 052 T0625-2000 |
| Ductility @ 15° C./cm | >150 | JTJ 052 T0624-1993 |
| Flash point (° C.) | 328 | JTJ 052 T0611-1993 |
| Fraass brittle point (° C.) | −17.5 | JTJ 052 T0613-1993 |
| Saturate, Aromatic, Resin and Asphaltene (SARA) fractions | | |
| Saturates (%) | 12.6 | |
| Aromatics (%) | 54.7 | JTJ 052 T0618-1993 |
| Resins (%) | 22.1 | |
| Asphaltenes (%) | 10.6 | |

TABLE 2

Physiochemical properties of Ras Tanura Saudi heavy crude oil.

| Test | Method | Result |
|---|---|---|
| API gravity | Calculated | 27.4 |
| Specific gravity 60/60 (1F) | ASTMD-1298 | 0.893 |
| Wax content (wt %) | UOP 46/64 | 5 |
| Asphaltene content (wt %) | IP 143/84 | 13 |
| Pour point (° C.) | IP 15/67 (86) | 18 |

TABLE 3

Physiochemical properties of Ras Tanura Saudi medium crude oil.

| Test | Method | Result |
|---|---|---|
| API gravity | Calculated | 30.8 |
| Specific gravity 60/60 (1F) | ASTMD-1298 | |
| Wax content (wt %) | UOP 46/64 | |
| Asphaltene content (wt %) | IP 143/84 | 6 |
| Pour point (° C.) | IP 15/67 (86) | |

Preparation Method
Preparation of Asphaltene Carboxylic (ACA) and Acid Chlorides Method 1: Asphaltene flakes separated from bitumen, sludge and crude oil (1.00 g) and concentrated sulfuric acid (25 mL, >95% w/w) were combined and stirred at 0° C. KMnO$_4$ (3 g) was added slowly under vigorous agitation, so that the temperature of the reaction mixture never exceeded 20° C. After this, the reaction mixture was heated at 30-80° C. for 30 minutes. Distilled water (50 mL) was then added and the solution stirred for a further 15 minutes at 60-110° C. The brown mixture was then diluted by the addition of 175 mL of water followed by a dropwise addition of 10 mL of 30% v/v hydrogen peroxide. The yellow-green mixture was filtered, washed with 150 mL of 10% aqueous HCl and allowed to dry. The dry powder was dispersed in 200 mL of distilled water via ultrasonication for 90 minutes. The dispersion was then centrifuged at 3000 rpm for 40 minutes and decanted to isolate the reaction products.

Method 2: Asphaltene (2 g) and 1.5 g of maleic anhydride (MA) were dissolved in 50 ml of toluene in three-necked bottom flask. The mixture was refluxed for 8 h under nitrogen atmosphere, followed by removing of solvent under reduced pressure to obtain asphaltene/maleic anhydride adducts (AMA).

Method 3: The asphaltene carboxylic acid obtained from method 1 (ACA) or method 2 AMA (3 g) was mixed with thionyl chloride (SOCl$_2$, 100 ml) under stirring and refluxed for 12 hrs. The solids were separated by filtration and washed with n-heptane several times and subsequently dried under vacuum at room temperature to obtain asphaltene acid chloride (As—COCl).

Preparation of Ethoxylated Quaternized Alkyl Pyridinium Salts

The 4-AP (0.01 mol), DDE (0.01 mol), PEG (0.01 mol) and NaOH powder were mixed in the presence of xylene as solvent and refluxed for 4 hrs from 100 to 180° C. The solid powder separated by filtrations and the xylene solvent evaporated under reduced pressure. The PEG was desalted by using hot saline water and the remained organic layer evaporated to obtain 4-ethylated-4-amino pyridine (EAP).

EAP (0.02 mol) was dissolved in dimethylformamide (DMF) (100 mL) and alkyl bromides (R—Br) based on pentyl, hexyl, heptyl, octyl, dodecyl, tetradecyl, octadecyl and docosyl bromide (R—Br; 0.02 mol) was added dropwise to the solution under stirring and reaction temperature ranged from 50 to 150° C. for reaction times ranged from 4 to 24 hrs. The DMF was evaporated and the products were recrystallized from ethanol to obtain quaternized ethoxylated alkyl pyridinium bromide (QEAP).

The bromide ion of QEAP (0.1 mol) was replaced and exchanged by different salts (0.1 mol) such as ammonium acetate (CH$_3$COONH$_4$), potassium cyanate (KOCN), sodium phosphate (NaH$_2$PO$_4$), NaHSO$_4$, NH$_4$SCN, NaNO$_3$, NaPF$_6$, HBF$_4$, KHCO$_3$ and lithium (bistrifuoromethylsulfon) imide (CF$_3$SO$_2$)$_2$NLi using an acetone or ethanol solvent at room temperature after removal of the precipitated salts. The BP was replaced with CH$_3$COO, OCN, H$_2$PO$_4$, HSO$_4$, SCN, NO$_3$, PF$_6$, BF$_4$, HCO$_3$, and (CF$_3$SO$_2$)$_2$N anions to obtain different anions (QAP-S) which have melting temperatures ranging from 40 to 85° C. The ethoylated-4-amino pyridinium cations neutralized with different anions having different melting temperatures below 100° C. confirm that they are forming ILs rather than cationic amphiphiles.

Amphiphilic Asphaltene Ionic Liquids (AILs)

Method 4: As—COCl (2 mmol, 0.28 g) and QAP-S (QEAP as example; scheme 2) (2 mmol) were dissolved in toluene (50 mL) in an ice bath in which the temperature ranged from −5° C. to 10° C. Triethylamine (TEA, 2 mmol) was added to the reaction mixture and the reaction temperature was kept at 10-25° C. for times ranging from 10 to 24 hrs. The reaction product was separated after evaporation of solvent and precipitation into heptane to obtain AIL.

Method 5: AMA (5 mmol, 1.06 g) and QAP-S (5 mmol) were dissolved in chloroform (50 mL) and 1-ethyl-3-(3-dimethylaminopropyl)carbodiimide (EDC) (0.04 g) was added to the reaction mixture. The reaction mixture temperature was kept at 10-25° C. for different times ranging from 10 to 24 hrs. The reaction product was isolated after evaporation of solvent and precipitation into heptane to obtain As-ILs.

Characterization

Fourier transform infrared (FTIR; Shimadzu FTIR 8000 spectrometer using KBr disc) was used to confirm the formation of the asphaltene ILs. $^1$H and $^{13}$C-NMR spectra of the synthesized PILs were obtained using a 400 MHz Avance DRX-400 spectrometer (Bruker, Billerica, USA). Surface tension was determined based on the pendant drop technique using the drop shape analyzer model DSA-100 (Kruss GmbH, Hamburg, Germany). Zeta potentials of emulsion samples were determined using Zetasizer Nano ZS; Malvern Instruments, Malvern, UK) at 25° C. An Olympus BX-51 microscope with a 100 W mercury lamp was used to investigate the emulsion and the dispersed crude oil droplets.

Thermal stability and characteristics were evaluated using thermogravimetric analysis (TGA; Shimadzu DTG-60M) and conducted under a nitrogen atmosphere at a heating rate of 10° C. per minute.

Dynamic light scattering (DLS; Zetasizer Nano) was used to determine the particle size hydrodynamic diameter (nm) and polydispersity index (PDI) in a toluene solution at 25° C. Zeta potentials (mV) of ILs and asphaltenes were determined after dispersion of their ethanol solution in aqueous water containing 0.001 M $NaNO_2$ at 25° C.

Application of Asphaltene Ionic Liquids (As-ILs) as Demulsifiers

Water-in-oil emulsions collected in the field were free of demulsifier. Shortly after collection, samples were drained of any free water. Free water is defined as water that separates rapidly and is not emulsified. All emulsions were prepared with a total volume of 50 mL. The ratio between crude oil and the aqueous phase (seawater) was in the range of 10-50 vol %. The emulsions were prepared by mixing using a Silver stone homogenizer. In a 500 ml beaker, the crude petroleum was stirred at 35° C. (9000 rpm for 30 min) while seawater was added gradually until the two phases became homogenous. The ratios of crude oil:water were 90:10, 80:20, 70:30 and 50:50.

The bottle test is used to estimate the capability of the synthesized demulsifiers to break water in oil emulsions. Demulsification was studied 60° C. or 65° C. using gravitational settling with graduated cylinders. The synthesized PILs solutions were injected into the emulsion using a micropipette. After the contents in the tube had been shaken in an oscillating shaker for 1 min, the cylinder was placed in a water bath at 60° C. or 65° C. to allow the emulsion to separate. The phase separation was recorded as a function of time. The interface between the emulsion and separated water phase can be easily observed during the settling process. The demulsification efficiency (DE %) can be calculated from the following equation:

$$DE\% = \frac{V_0 \times 100}{V_1} \quad (1)$$

where $V_o$ and $V_1$ are the volume of emulsified and separated water, respectively.

Characterization of Amphiphilic Asphaltene ILs

Figure 2:
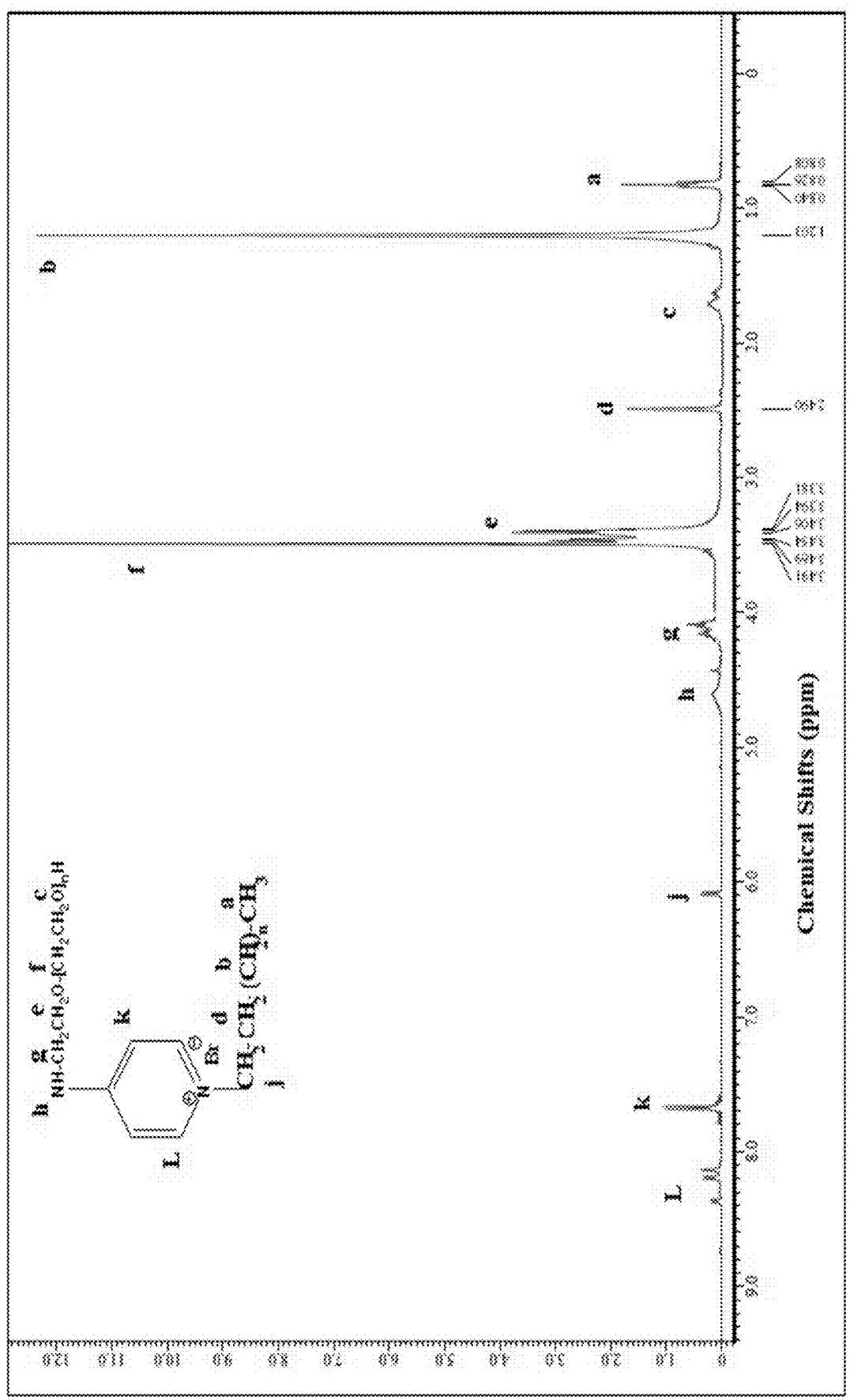
FIG. 2. HNMR spectrum of QAP-Br.
Figure 3:
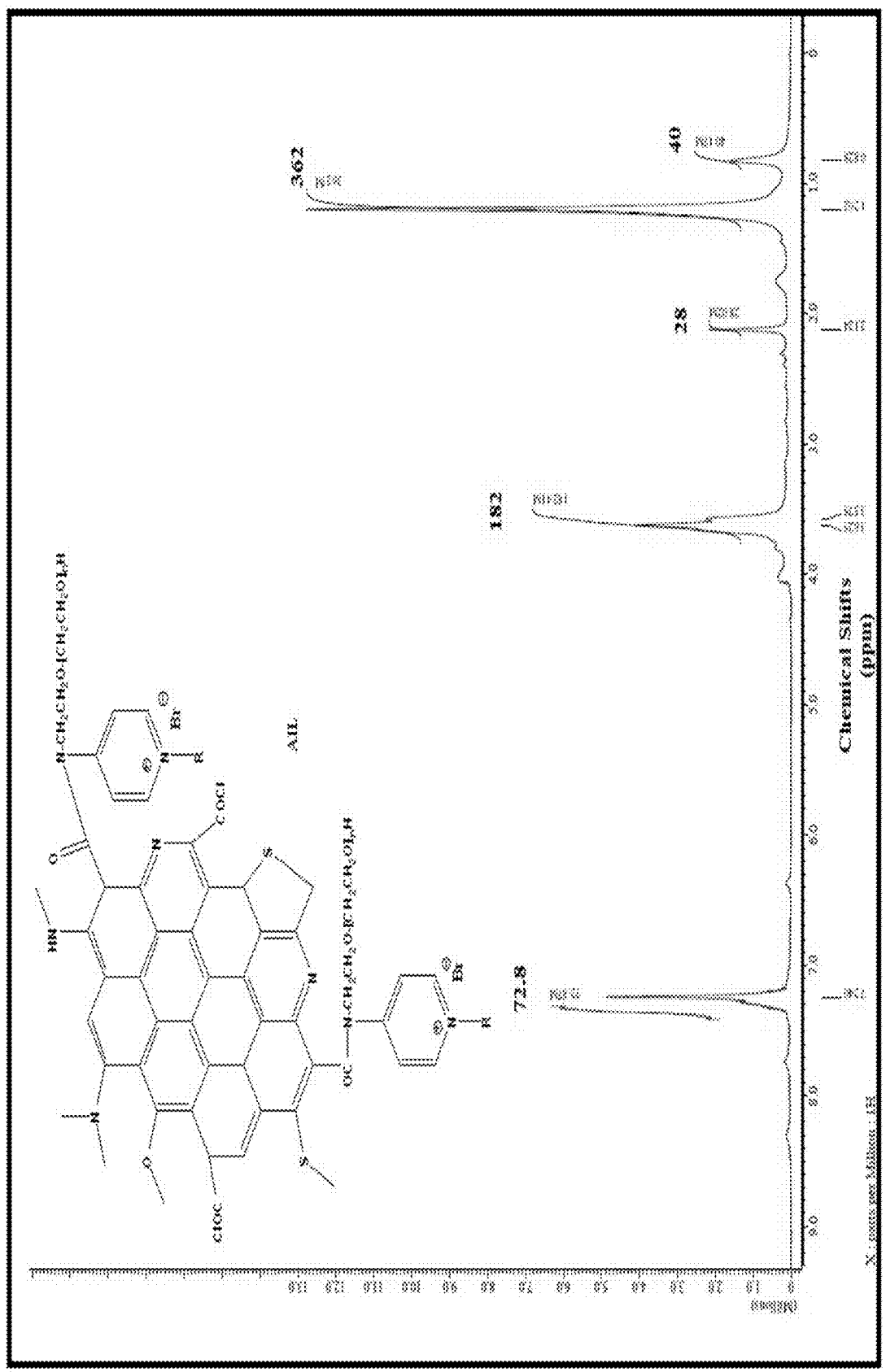
FIG. 3. HNMR spectrum of AIL-1.
Figure 4:
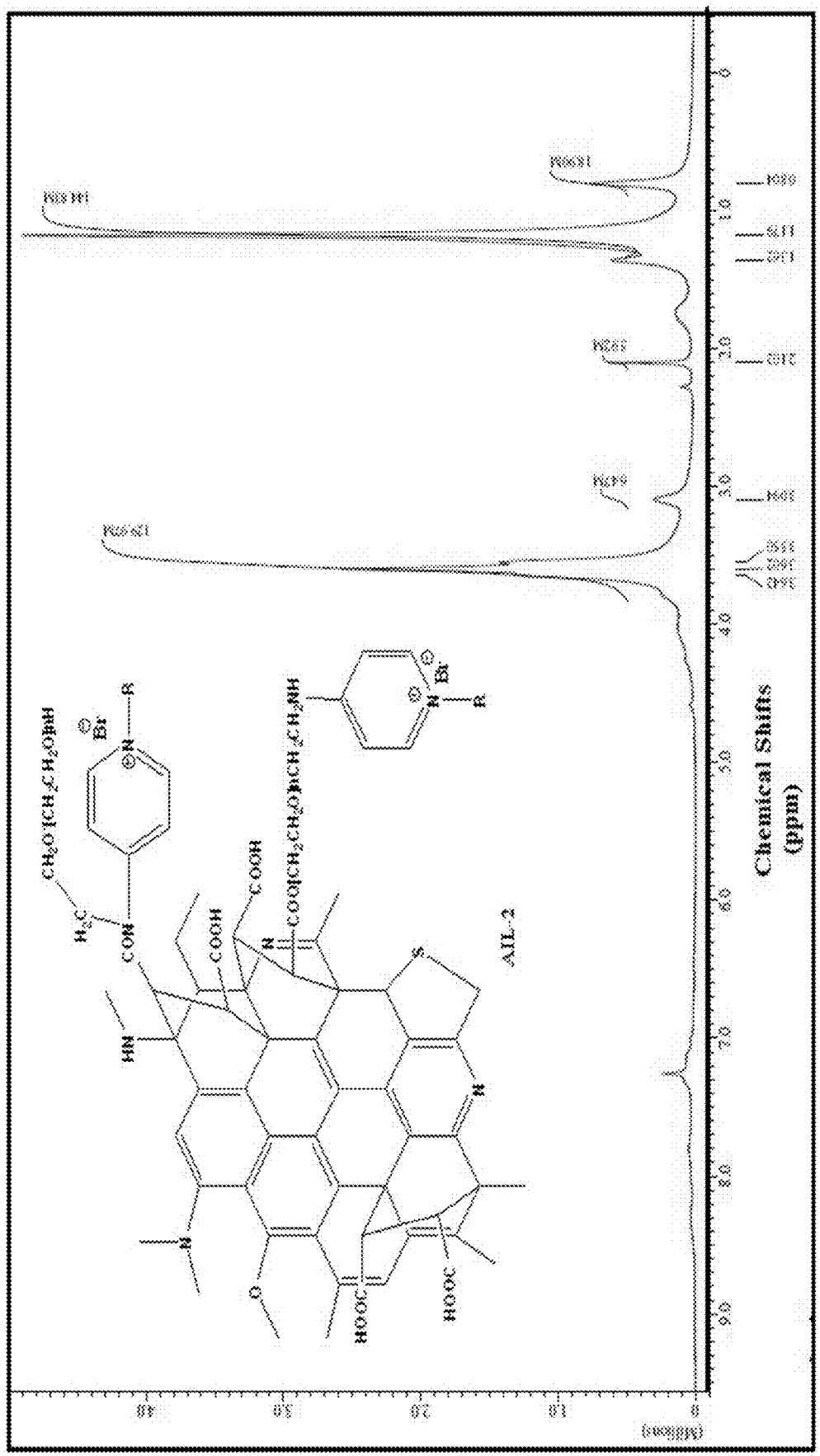
FIG. 4. HNMR spectrum of AIL-2.

The chemical structures of the asphaltenes, QEAP, and AILs were elucidated from $^1$HNMR spectra represented in FIGS. 1-4. The $^1$HNMR spectrum of FIG. 1 confirms that the chemical structure of asphaltenes contains a significant quantity of paraffinic H atoms ($CH_3$, $CH_2$), relatively low amount of monoaromatic and polyaromatic H atoms (5%), and a negligible percentage of olefins. The $^1$HNMR spectrum of FIG. 2 shows that the chemical structure of QEAP has peaks at 8.3, 6.1, 4.6, 3.5 and 0.84 ppm that indicate aromatic (H), +N—$CH_2$, +N—C—$CH_2$, $OCH_2CH_2$— and $CH_3$ protons of QEAP. The disappearance of a broad peak at 4.6 ppm related to NH (FIG. 2) and appearance of a strong peak at 7.24 ppm in the AIL type 1 spectrum (FIG. 3) elucidated that the formation of amide groups between QEAP and As—COCl to produce AIL. It is also elucidated that from the HNMR spectrum of AIL (FIG. 3) that the integration ratios of peak appearing at 0.8 and 1.2 ppm related to $(CH_2)_n$ and $CH_3$ of alkyl chains of QEAP. In addition, there is no any additional $CH_3$ or $CH_2$ groups added from As—COCl and this confirms that all alkyl groups of asphaltene (FIG. 1) converted to acid chloride. Moreover, the higher integration of peak at 7.2 ppm of As—COCl (FIG. 3) than that determined in HNMR spectrum of QEAP confirms the incorporation of polycondensed aromatics of asphaltene in the chemical structure of AIL-2. The proposed chemical structure of AIL-2 represented in Scheme 3 was confirmed from its $^1$HNMR spectrum represented in FIG. 4. The intensity of peaks at 1.2 ppm (S, $CH_2$ aliphatic protons), and 7.26 ppm (S, aromatic protons) in AIL-2 prepared by method 5 (FIG. 4) elucidates the decreasing of aromatic hydrocarbon intensity more than aliphatic intensity to confirm the reaction of QEAP with AMA or ACA. The increasing of $OCH_2$—$CH_2$ integration in the spectrum of AIL-2 (FIG. 4) more than AIL-1 (FIG. 3) elucidates the higher reactivity of QEAP towards AMA to form amide or ester groups (scheme 3). The appearance of peaks at 3.09 ppm in spectrum of AIL-2 (FIG. 4) elucidate the esterification of QEAP hydroxyl groups with anhydride groups of AMA.

Figure 5:
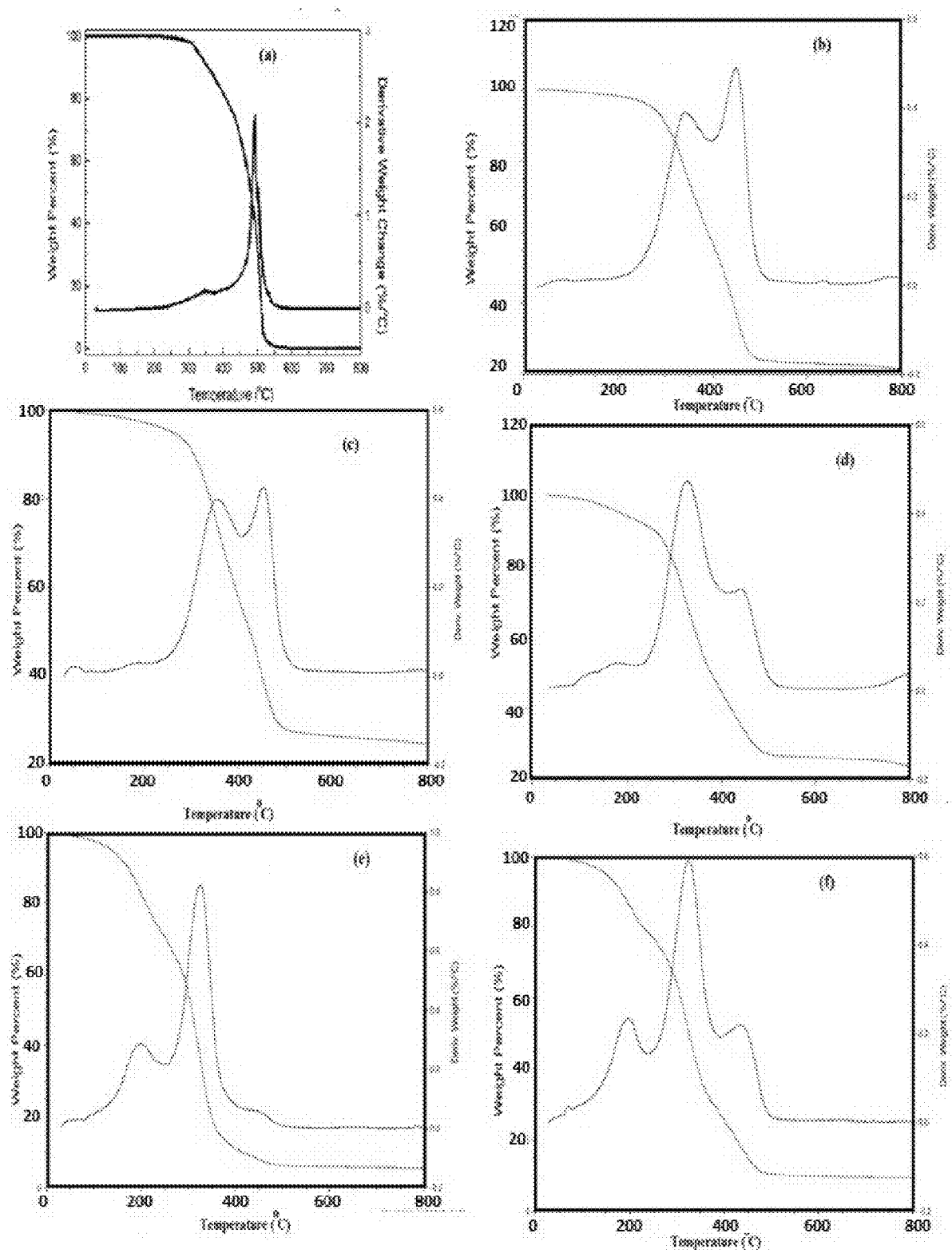
FIG. 5. TGA and DTA thermograms in panels a-f of a) asphaltenes, b) AMA, c) ACA, d) QAP-Br, e) AIL-1 and f) AIL-2.
Figure 7:
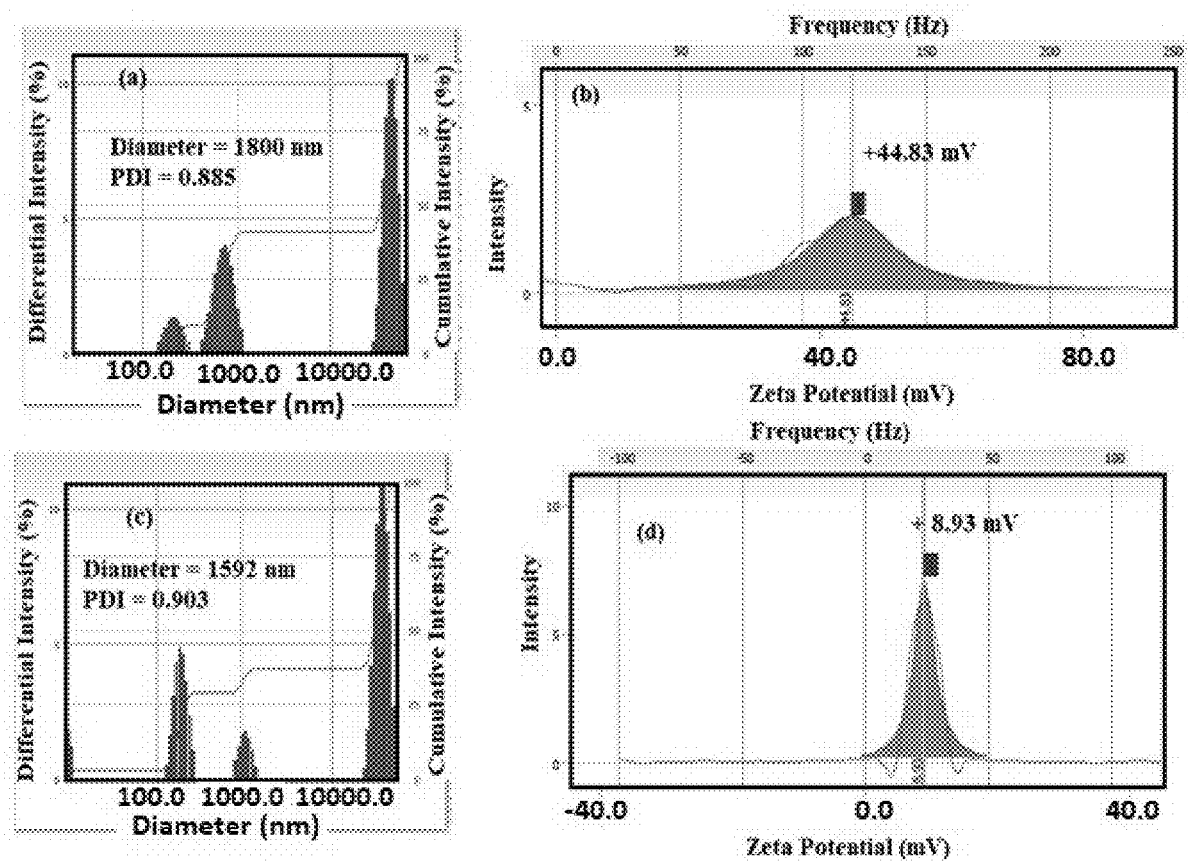
FIG. 7. DLS and zeta potential data in panels a-d of a), b) AIL-1, c) and d) QAP-Br in aqueous solution.

It is important to study the thermal stability of the prepared ILs before application as oilfield chemicals because the petroleum industry usually needs to expand their operations at elevated temperature. The data of thermogravimetric and differential thermogravimetric thermograms (TG-DTG) of asphaltenes, AMA (method 2), ACA (method 1), QEAP, AIL (method 4) and AIL-2 (method 5), are presented in FIG. 5A-F, respectively. The data show that the thermal stability of asphaltene (FIG. 5A) was increased after modification to AMA (FIG. 5B) and ACA (FIG. 5C). Asphaltenes, AMA, ACA were degraded at 173° C., 250° C., and 290° C., respectively. Moreover, in the temperature range of 367-600° C. there is a drastic decomposition of native asphaltenes (75.5 Wt. %), AMA (65 Wt. %), and ACA (60 Wt. %) that is accompanied by endothermic and exothermic effects and elimination of water $H_2O$, and carbon dioxide $CO_2$. AMA and ACA are transformed into coke due to the formation of cyclic derivatives (pyrolysis: elimination of nitrogen $N_2$, ethylene $C_2H_4$, and ethyl $CH_3$—$CH_2$—) [13]. It was also noted that the thermal stability of AIL-1 (FIG. 5E) and AIL-2 (FIG. 5G) shows a new additional peak at 450° C., which also appeared in QEAP thermogram (FIG. 5D) to confirm the reaction of As—COCl or AMA with QEAP. The AIL (FIG. 5E) and AIL-2 (FIG. 5G) thermograms contain three to five temperature transitions, namely, the elimination of water molecules adsorbed on the surface and in the bulk of native asphaltenes, As—COCl or AMA and QEAP; the section corresponding to the evolution of carbon dioxide gases; and the section of the transformation of AIL (FIG. 5E) and AIL-2 (FIG. 5F) in coke. Esterification or amidation of ACA or As—COCl or AMA with QEAP leads to the increase in thermal stability of QEAP, which is related to the formation of new strong chemical bonds and replacement of hydrogen by new modified asphaltene functional groups [14]. The AIL (FIG. 5E) and AIL-2 (FIG. 5G) thermograms indicated that their mass losses were completed in a three step. The sample keeps thermostable below 200° C. It begins to lose weight at about 210° C., reaches the maximum rate of weight loss at 320° C. and completely loses its weight when the temperature reaches 430° C. which similar to alkyl pyridinium bromide ionic liquids [15].

Surface Activity of Amphiphilic Asphaltene ILs

Figure 6:
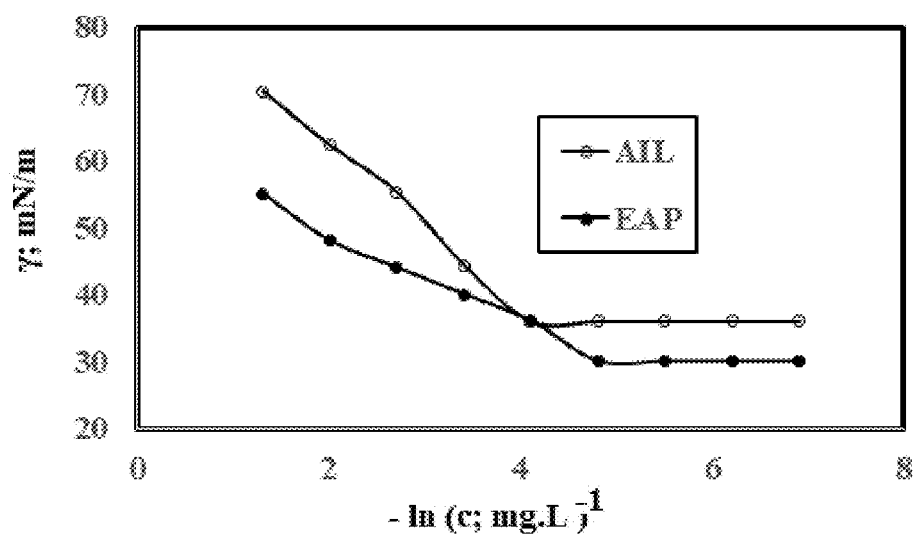
FIG. 6. Relation between surface tension and different concentrations of QAP-Br and AIL-1 at 25° C.

Most of the chemicals used in the oilfield industry have surface activity. This activity refers to the amphiphilic character of these chemicals. Different surface activity parameters such as surface tension, interfacial tension and surface activity of the prepared QEAP, AIL and AIL-2 in water and on the surface of sandstone rock were investigated. The presence of different active sites in the chemical structure of QEAP, AIL and AIL-2 affect their performance in aqueous solution. It was noticed that the AIL-2 did not soluble in water but it was soluble in alcohol. This can be referred to esterification of hydroxyl groups of QEAP with AMA (Scheme 3) that reduced the hydrophilicity of AIL-2. Accordingly, the surface activities of QEAP and AIL was measured in water at 25° C. from the surface tension measurements. The relation between surface tension data of QEAP and AIL at different concentrations used to determine the aggregation and adsorption parameters. In this respect, the relation between the equilibrium surface tension data ($\gamma$; mN/m) of QEAP and AIL and their concentrations (ln c, mg/L) at 25° C. is represented in FIG. 6.

The critical micelle concentrations (cmc; mg/L), determined at the concentration that $\gamma$ is started to increase, and the corresponding surface tension at cmc ($\gamma_{cmc}$) are detected and tabulated in Table 4. The data listed in Table 4 confirmed that the solubility of QAP-Br in water reduced by the reaction with the hydrophobic moieties of asphaltene by reacting with As—COCl with QEAP (method 4) to produce AIL that indicated from lowering cmc from 125 to 62.5 mg/L for QEAP to AIL, respectively. The surface tension at cmc ($\gamma$cmc) data represented in Table 4 confirmed that the QEAP reduced the water surface tension more than AIL which seems reasonable to propose that the hydrophobic group of asphaltene unfolding of surface tails and loops to cover the entire interface and oriented and packed their adsorption at the air/water interface. These data were confirmed from DLS data measurements for QEAP and AIL to evaluate the aggregation diameter and their surface charges (zeta potentials; mV) as represented in FIG. 7A-D. The data confirmed that the aggregation diameter of the AIL (FIG. 7a) and surface charges (FIG. 7b) were 1800 and 44.83 mV, which changed from 1592 nm (FIG. 7) and +8.93 mV (FIG. 7d) for QEAP, respectively. These data agree with cmc data to confirm that the presence of asphaltene in the chemical structure of AIL increases the hydrophobic interaction of QEAP and increases the micelle diameter and their positive charges due to the presence of pyrridinium cations.

AIL molecules adsorbed per unit area of the interface is designated as surface excess concentration ($\Gamma_{max}$). It can be calculated from equation (3):

$$\Gamma_{max} = \frac{1}{RT} \times \left(\frac{-\partial \gamma}{\partial \ln c}\right)_T \quad (3)$$

where R and T are constant equals 8.314 J mol$^{-1}$ K$^{-1}$ and temperature (K) of measurements, respectively. The relation between $A_{min}$ and $\Gamma_{max}$ is shown in equation (4)

$$A_{min} = \frac{10^{16}}{N\Gamma_{max}} \quad (4)$$

where N is Avogadro's number. is used to calculate Amin which summarized in Table 4. The Amin was used to determine the orientation and packing degrees of the adsorbed QAP-Br and AIL molecules, at the interfaces. The increment of $\Gamma_{max}$ value for AIL, Table 4, indicated the increment of AIL concentration adsorbed at the air/water interface which also reflected on a reduction of water surface tension.

The increment of $\Gamma_{max}$ value for AIL can be referred to the interactions between the hydrophilic asphaltene arms of AIL molecules that increase the packing of molecules at interfaces. The low $A_{min}$ (0.033 nm$^2$/molecule) obtained for AIL suggests its adsorption which oriented away from the liquid in a more tilted position. However, the complete surface coverage of AIL chains with the flexible air/water interface was confirmed from low Amin and high $\Gamma_{max}$ values.

The solubility of QEAP, AIL and AIL-2 in water indicated that the AIL-2 cannot soluble in water. In this respect, the relative solubility number (RSN) of the prepared QEAP, AIL and AIL-2 were determined and listed in Table 4. It was determined as 1 gram of the prepared materials was solubilized in 30 ml solution consisting of 96 wt %-dioxane and 4 wt %-toluene and titrated against water until turbid solutions occurred. The RSN value is a number, where a higher number of more than 17 indicates a more water-soluble

TABLE 4

Surface activity parameters of QEAP and AILs in water at 25° C.

| Derivatives | Cmc (mg·L$^{-1}$) | $\gamma_{cmc}$ mN·m$^{-1}$ | $\pi_{cac}$ mN·m$^{-1}$ | $-\partial\gamma/\partial$ ln c | $\Gamma_{max} \times 10^{10}$ mol/cm$^2$ | $A_{min}$ nm$^2$/molecule | RSN (mL) |
|---|---|---|---|---|---|---|---|
| QEAP | 125 ± 0.3 | 30.2 ± 0.2 | 42 | 6.75 | 2.73 | 0.060 | 14.8 |
| AIL | 62.5 ± 0.5 | 36.2 ± 0.4 | 36 | 12.38 | 5.01 | 0.033 | 13.5 |
| AIL-2 | — | — | — | — | — | — | 10.3 |

The effectiveness of QEAP and AIL to reduce the surface tension (acmc) was calculated from the equation $$\pi_{cac} = \gamma_o - \gamma_{cac} \quad (2)$$

where $\gamma_0$ and $\gamma_{cac}$ are water surface tension (72.1 mN/m) and surface tension at cac, respectively. The greater $\pi$cac value of QAP-Br more than AIL indicates that the QAP-Br interacted with water via dipole-dipole interaction mechanism more than AIL. The adsorption of QAP-Br and AIL molecules at air/water interface is the alternative mechanism to prevent their micellization in the bulk solution. The ability of molecules to adsorb at air/water interface used to evaluate their surface activities. The concentration of QAP-Br and product while a more oil-soluble product has a lower number than 13. The RSN indicated that AIL can be solubilized in both polar and nonpolar organic solvents. These data confirm that the solubility of AIL in water is greater than AIL-2 which insoluble in water. This means that the esterification of the hydroxyl groups of PEG reduces the water solubility of AIL-2 in water due to the hydrophobic effect of their asphaltene phenyl groups.

Application of the Prepared AIL and AIL-2 as Demulsifier for Petroleum Crude Oil Emulsions Demulsifiers are the best oil-field chemicals that can be used to solve the petroleum crude oil emulsions, petroleum sludge and gas hydrates problems. The ability of demulsifier to adsorb at water/oil interfaces, replace the asphaltene rigid films at interfaces with the formation of soft film and reduction the interfacial tension are very important parameters. The present work aims to use asphaltene modified ionic liquids based on AIL and AIL-2 in the presence of QAP-s to replace the asphaltenes at oil water interfaces. The xylene/ethanol 75/25 (vol %) solvent was used to solubilize demulsifier mixtures based on AIL, AIL-2 and QAP-s. The demulsifier mixtures and codes were represented in Table 5.

TABLE 5

| code | Demulsifier composition Wt % AIL | AIL-2 | QAP-S | IFT (mN/m) Crude oil:Water 90:10 | 50:50 | 10:90 |
|---|---|---|---|---|---|---|
| M1 | 100 | 0 | 0 | 2.5 | 1.3 | 0.83 |
| M2 | 0 | 100 | 0 | 13.3 | 15.8 | 20.3 |
| M3 | 0 | 0 | 100 | 1.3 | 0.53 | 0.13 |
| M4 | 60 | 20 | 20 | 0.23 | 1.35 | 3.23 |
| M5 | 40 | 20 | 40 | 1.34 | 0.55 | 1.23 |
| M6 | 30 | 20 | 50 | 0.53 | 1.45 | 3.53 |
| M7 | 20 | 20 | 60 | 2.31 | 1.23 | 0.88 |

The interfacial tension (IFT; mN/m) between crude oil and water solutions of M1-M7 versus crude oil emulsions O/W were determined and listed in Table 5. The synthetic crude oil/water or W/O emulsions, ranged from 90:10 to 50:50, prepared in this study are W/O emulsions as indicated from drop test method that confirms that the outer phase is oil because it was completely dispersed in toluene. The data of IFT represented in Table 5 show that the interfacial tension (IFT) between crude oil emulsions and 1000 ppm of demulsifier aqueous solution water were reduced with increase the water contents in emulsions for individual surfactants. Moreover, the reduction of IFT varied with the demulsifier compositions from M4 to M7. The M7 (contain higher QAP-S contents) shows greater reduction in IFT with increasing of water contents of emulsion (O:W; 10:90). M6 and M4 show lowering in IFT for O:W emulsion (90:10). M5 shows a greater reduction in IFT values using W:O (50:50). These data elucidate that the stability of demulsifier composition s to brine water salt with a reduction of IFT value and confirm the demulsification of crude oils having high salt contents.

Different concentrations of demulsifier compositions ranged from 100 to 5000 ppm were used to demulsify the different crude oil emulsions using the conventional heating method as described in the experimental section. The DE (%) and the separation settling times were determined and listed in Table 6.

TABLE 6

Demulsification efficiencies and their times at different concentrations of M5-M7 for different crude oil emulsions at 65° C.

| Demulsifier | Conc. (ppm) | Demulsification data 90:10 DE % | 50:50 Time (min) | 10:90 DE % | Time (min) | DE % | Time (min) |
|---|---|---|---|---|---|---|---|
| M6 | 100 | 50 | 600 | 20 | 600 | 10 | 600 |
|  | 1000 | 80 | 400 | 30 | 500 | 20 | 480 |
|  | 5000 | 100 | 120 | 70 | 360 | 40 | 360 |
| M5 | 100 | 60 | 400 | 60 | 360 | 40 | 320 |
|  | 1000 | 70 | 360 | 80 | 240 | 50 | 280 |
|  | 5000 | 80 | 340 | 100 | 120 | 70 | 240 |
| M7 | 100 | 25 | 500 | 40 | 400 | 100 | 120 |
|  | 1000 | 30 | 450 | 60 | 350 | 100 | 100 |
|  | 5000 | 40 | 400 | 70 | 300 | 100 | 60 |

Figure 8:
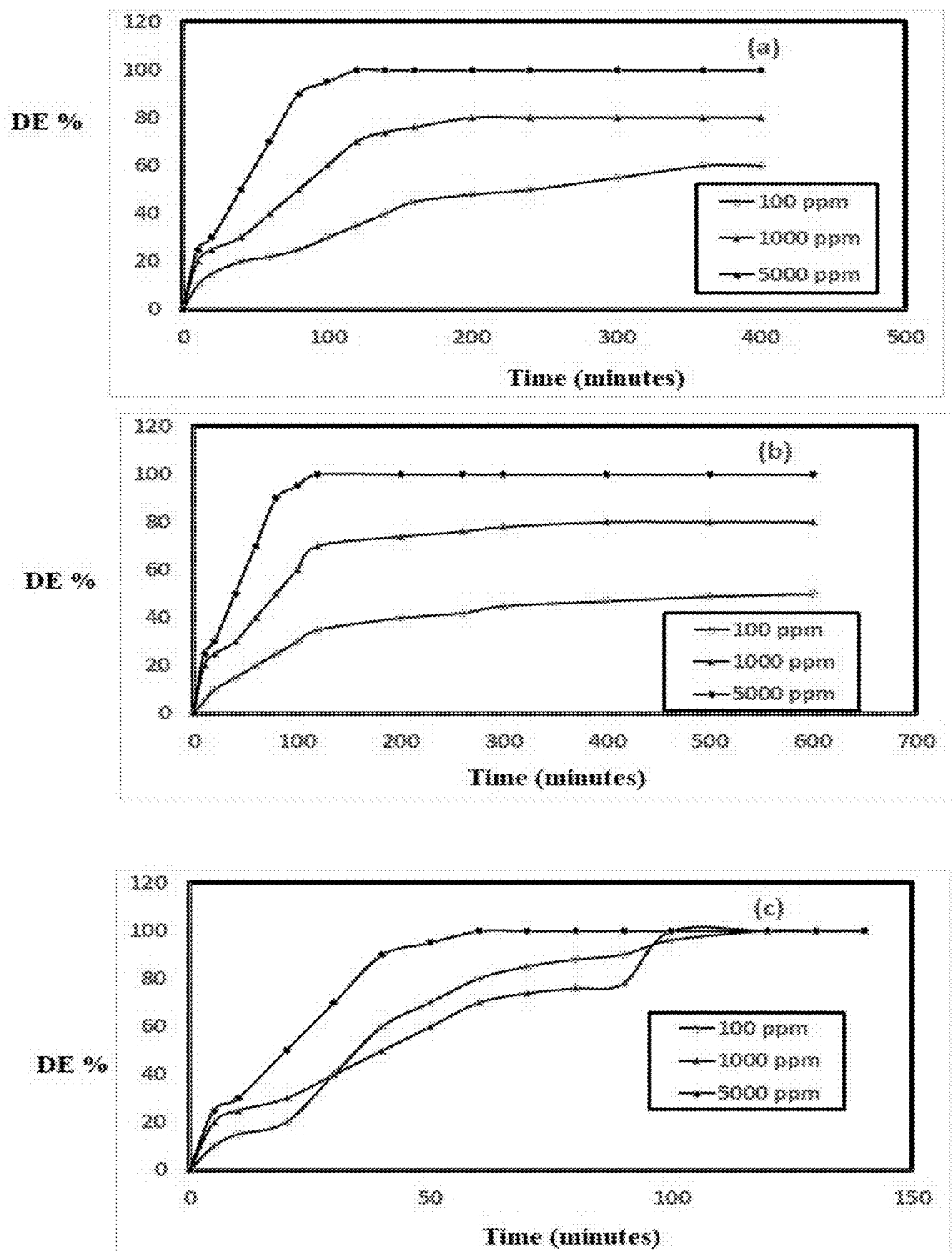
FIG. 8. Relation of DE % and demulsification times of different concentrations in panels a-c of a) M5 with emulsion 50:50, b) M6 with emulsion 90:10 and c) M7 with emulsion 10:90 (O:W) at 65° C.
Figure 9:
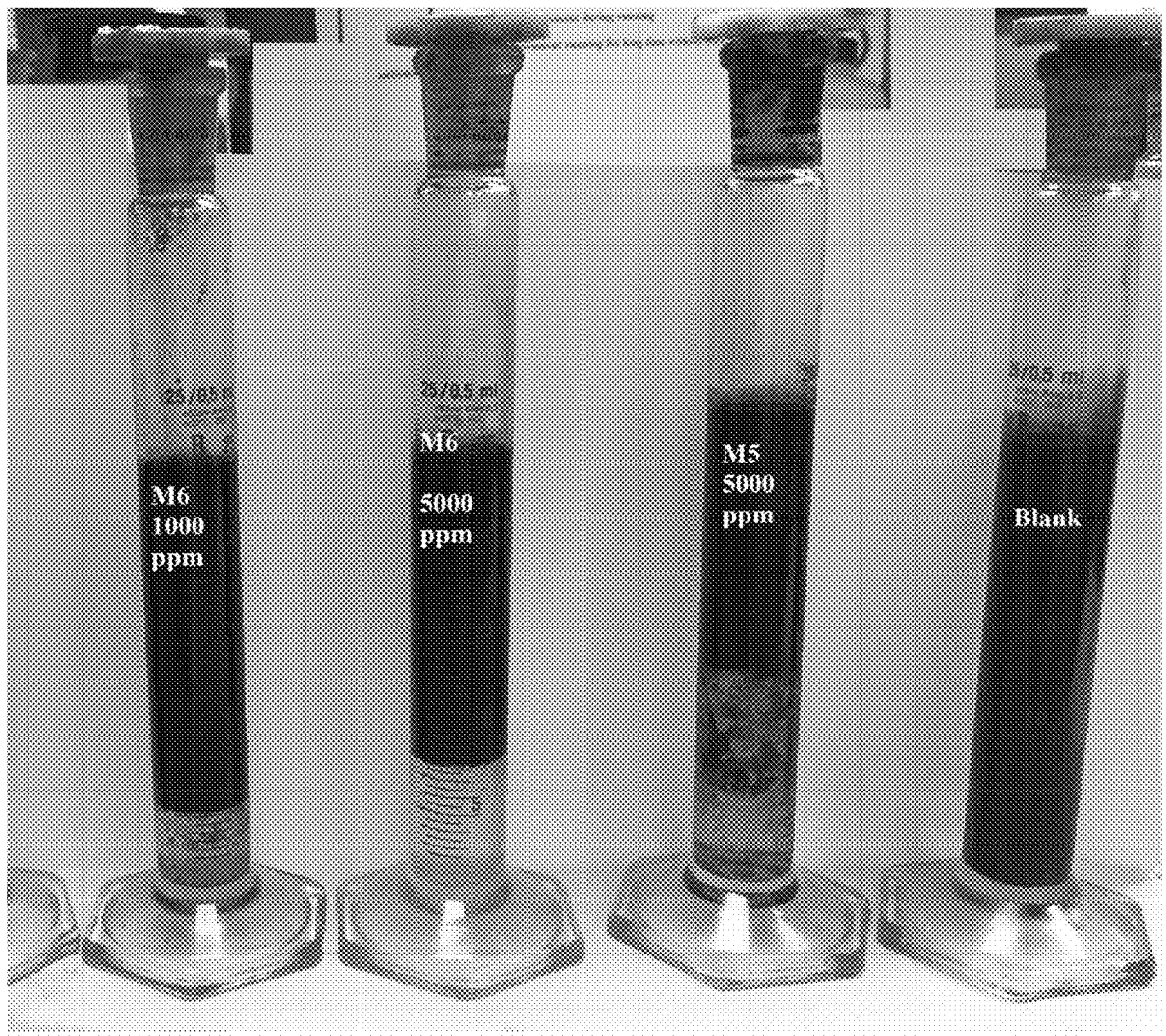
FIG. 9. Demulsification photos of petroleum crude oil-water emulsions in the presence of M5 and M6 and absence of demulsifier (blank).
Figure 10:
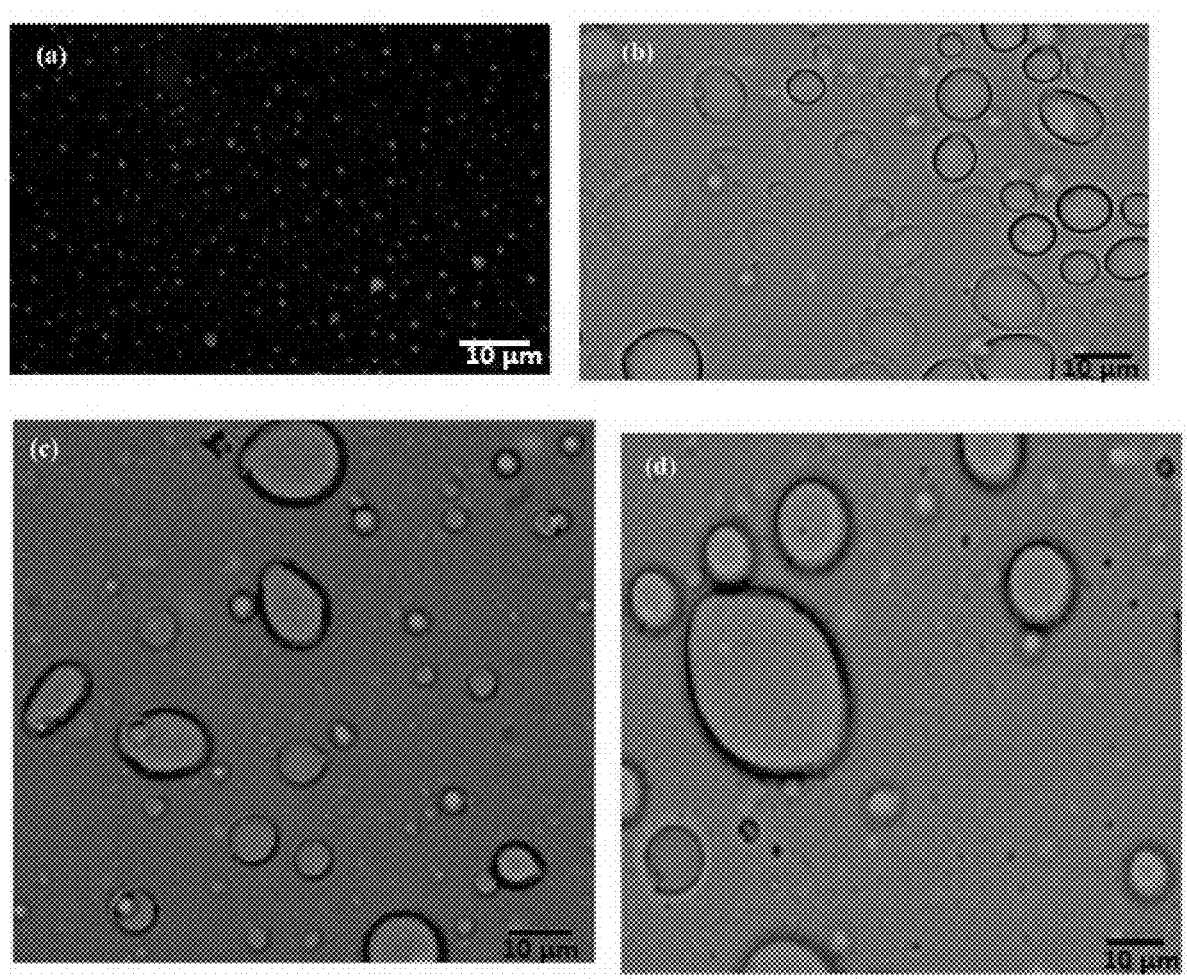
FIG. 10. Optical microscopic photo of crude oil-water emulsion (50:50) in panels a-d a) blank after 7 days, b) after injection with 100 ppm of M5, c) after injection with 1000 ppm of M5 and d) after injection with 5000 ppm of M5.

The relations between DE (%) and the separation time of crude oil emulsions using different concentrations of M5-M7 were represented in FIG. 8A-C. The photos of water separations of crude oil emulsions using M5-M7 were clarified in FIG. 9.

Careful inspection of data listed in Table 6 and FIG. 8a-c indicate that the DE (%) 100 occurred in the presence of 5000 ppm of M5, M6 and M7 for O:w emulsions 50:50, 90:10 and 10:90, respectively. The demulsification times of M5, M6 and M7 for O:w emulsions 50:50, 90:10 and 10:90, are 120, 120 and 60 minutes, respectively. Accordingly, the ability of M5-M7 to replace asphaltene layers at emulsion droplets controls the DE (%) data is affected by demulsifier compositions. The kinetics dehydration curves (FIG. 8A-C) of crude oil emulsions showed s-curves which indicated the demulsification mechanism of crude oil emulsions. The first stage depends on ILs diffusion, the second stage confirms the replacement of asphaltene films, the third stage represents dehydration and the last fourth stage clarifies dehydration equilibrium step. The first step depends on the diffusion of demulsifier ILs in the crude oil emulsions controls the rate of dehydration mechanism of demulsification process [16]. The effect of M5 demulsifier concentrations on the emulsion droplet was evaluated by an optical microscope and represented in FIG. 10A-D.

However, it can also expected that because of the strong bridging interaction and charging neutralization between the AIL, AIL-2 and QAP-S cations and anion with the heteroatoms of asphaltene macromolecules, the protective film surrounds water droplet was partially destroyed and replaced with AIL or AIL-2. At this point, the asphaltene layers start moving away from the water droplet surface and more AIL or AIL-2 interact with water droplets. The new AIL or AIL-2 interfacial films provide an excellent site for the aggregation of the small water droplets. The dipole-dipole interaction and hydrogen bonds between hydrophilic moieties of AIL or AIL-2 make the water droplets close contact, the water droplets finally coalesce to form big ones to separate by gravity force from crude oil-water emulsions. The ability of AIL or AIL-2 to aggregate the asphaltene with a small size will generate more voids on the water droplet, making it easier for the AIL or AIL-2 macromolecule to interact with the water droplet surface and facilitating the demulsification process.

All demulsifiers cannot separated from the crude oil in the oilfield, but it can affect the refining process. The prepared AIL, AIL-2 and QAP-S cannot be recycled but their structures are based on asphaltenes that were compatible with the crude oil and do not affect the catalytic refining operation.

Funding Statement:

This project was funded by the National Plan for Science, Technology and Innovation (MAARIFAH)—King Abdulaziz City for Science and Technology—the Kingdom of Saudi Arabia—award number (13-PET175-03). The authors also, acknowledge with thanks Science and Technology Unit, King Abdulaziz University for technical support.

REFERENCES

[1] Jerome Panzer, R. P., N.J. Combination of Asphaltenes with Flow Improver Polymers to Improve the Flow Properties of High Boiling Fuel Oils. U.S. Pat. No. 4,074,978 (A), 1978.
[2] Willem P. C. Duyvesteyn, R. L. M. Oxidation of Asphaltenes. U.S. Pat. No. 7,811,444 B2, 2010.

[3] Deeds, P. J. C. M. H. W. C. T. Process for Separating and Converting Heavy Oil Asphaltenes in a Field Location. U.S. Pat. No. 4,514,283, 1985.
[4] Thomas F. Derosa, R. L. S., Benjamin J. Kaufman, Eugene M. Jao Compatibilization of Asphaltenes in Bituminous Liquids Using Bulk Phosphoamination U.S. Pat. No. 5,132,005, 1992.
[5] Ovalles, C.; Rogel, E.; Morazan, H.; Moir, M. E., Synthesis, Characterization, and Mechanism of Asphaltene Inhibition of Phosphopropoxylated Asphaltenes. *Fuel* 2016, 180, 20-26.
[6] Abdullah, M. M. S.; Al-Lohedan, H. A.; Atta, A. M., Novel Magnetic Iron Oxide Nanoparticles Coated with Sulfonated Asphaltene as Crude Oil Spill Collectors. *RSC Advances* 2016, 6 (64), 59242-59249.
[7] Yakubov, M. R.; Gryaznov, P. I.; Yakubova, S. G.; Tazeeva, E. G.; Mironov, N. A.; Milordov, D. V., Structural-Group Composition and Properties of Heavy Oil Asphaltenes Modified with Sulfuric Acid. *Petroleum Science and Technology* 2016, 34 (22), 1805-1811.
[8] Armin C. Pitchford, B., Okla, Phillips Petroleum Company Asphaltene-Derived Surfactant Composition and Its Preparation. U.S. Pat. No. 3,646,120, 1972.
[9] Will A. Ledoux, W. S., Atul Kumar Asphaltenes as Sacrifical Agents in Oil Recovery Processes. U.S. Pat. No. 4,113,013, 1978.
[10] Jorge, M.-H. J.-A. a. A., *Ionic Liquids: Applications and Perspectives; Current Knowledge and Potential Applications of Ionic Liquids in the Petroleum Industry.* 2011.
[11] Eugenio Alejandro Flores Oropeza, L. V. C. S., Alfonso Lopez Ortega, José Gonzalo Hernández, Fernando Alvarez Ramirez, Arquimedes Estrada Martinez, Flavio Salvador Vázquez Moreno Synergistic Formulations of Functionalized Copolymers and Ionic Liquids for Dehydrated and Desalted of Medium, Heavy and Extra Heavy Crude Ols. U.S. Pat. No. 9,587,182 B2, 2017.
[12] Sakthivel, S.; Gardas, R. L.; Sangwai, J. S., Effect of Alkyl Ammonium Ionic Liquids on the Interfacial Tension of the Crude Oil-Water System and Their Use for the Enhanced Oil Recovery Using Ionic Liquid-Polymer Flooding. *Energy & Fuels* 2016, 30 (3), 2514-2523.
[13] Gonçalves, M. L. A.; Teixeira, M. A. G.; Pereira, R. C. L.; Mercury, R. L. P.; Matos, J. R., Contribution of Thermal Analysis for Characterization of Asphaltenes from Brazilian Crude Oil. *Journal of Thermal Analysis and calorimetry* 2001, 64 (2), 697-706.
[14] Gryaznov, P. I.; Yakubova, S. G.; Tazeeva, E. G.; Milordov, D. V.; Yakubov, M. R., Thermal Stability and Sorption Properties of Asphaltene Sulfocathionites. *Petroleum Science and Technology* 2018, 36 (22), 1837-1842.
[15] Tong, B.; Liu, Q.-S.; Tan, Z.-C.; Welz-Biermann, U., Thermochemistry of Alkyl Pyridinium Bromide Ionic Liquids: calorimetric Measurements and Calculations. *The Journal of Physical Chemistry A* 2010, 114 (11), 3782-3787.
[16] Ezzat, A. O.; Atta, A. M.; Al-Lohedan, H. A.; Hashem, A. I., Synthesis and Application of New Surface Active Poly (Ionic Liquids) Based on 1,3-Dialkylimidazolium as Demulsifiers for Heavy Petroleum Crude Oil Emulsions. *Journal of Molecular Liquids* 2018, 251, 201-211.

While the invention has been described in terms of its preferred embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

The invention claimed is:

1. A method of stabilizing petroleum crude oil, comprising combining a petroleum crude oil with a quantity of an amphiphilic asphaltene ionic liquid, wherein the quantity of amphiphilic asphaltene ionic liquid is sufficient to prevent aggregation and precipitation of asphaltenes from the petroleum crude oil, thereby stabilizing the petroleum crude oil.

2. The method of claim 1 wherein the amphiphilic asphaltene ionic liquid comprises one or more asphaltene quaternary aminopyridine salts.

3. The amphiphilic asphaltene ionic liquid of claim 2 wherein the one or more asphaltene quaternary aminopyridine salts include one or more of

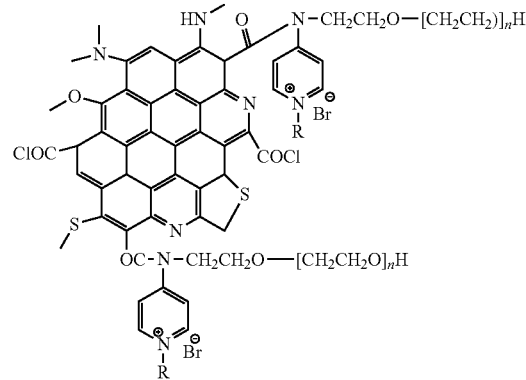

and

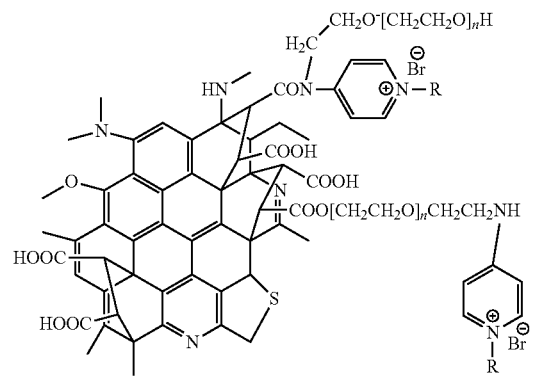

and
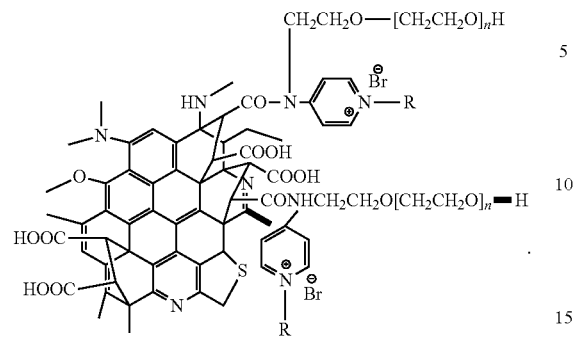
* * * * *

UNITED STATES PATENT AND TRADEMARK OFFICE
CERTIFICATE OF CORRECTION

PATENT NO. : 10,907,107 B1  
APPLICATION NO. : 16/894975  
DATED : February 2, 2021  
INVENTOR(S) : Ali Issa Ismail et al.

Page 1 of 1

It is certified that error appears in the above-identified patent and that said Letters Patent is hereby corrected as shown below:

On the Title Page

Item (72) the residence information of the following inventors should read:  
Ayman Mohamady Atta, Riyadh (SA)  
Mohamed Hassan El-Newhy, Riyadh (SA)

Signed and Sealed this  
Twenty-third Day of March, 2021

Drew Hirshfeld  
*Performing the Functions and Duties of the*  
*Under Secretary of Commerce for Intellectual Property and*  
*Director of the United States Patent and Trademark Office*